(12) United States Patent
Song

(10) Patent No.: US 9,693,807 B2
(45) Date of Patent: Jul. 4, 2017

(54) SPINAL COMPRESSOR AND DISTRACTOR

(71) Applicant: John Song, Chicago, IL (US)

(72) Inventor: John Song, Chicago, IL (US)

( * ) Notice: Subject to any disclaimer, the term of this patent is extended or adjusted under 35 U.S.C. 154(b) by 181 days.

(21) Appl. No.: 14/659,115

(22) Filed: Mar. 16, 2015

(65) Prior Publication Data

US 2015/0250504 A1   Sep. 10, 2015

Related U.S. Application Data

(63) Continuation-in-part of application No. 14/200,785, filed on Mar. 7, 2014, now Pat. No. 9,323,670.

(51) Int. Cl.
| A61B 17/58 | (2006.01) |
| A61B 17/60 | (2006.01) |
| A61F 2/00 | (2006.01) |
| A61B 17/70 | (2006.01) |

(52) U.S. Cl.
CPC ........ *A61B 17/7014* (2013.01); *A61B 17/708* (2013.01); *A61B 17/7079* (2013.01)

(58) Field of Classification Search
CPC .......... A61B 17/025; A61B 2017/0256; A61B 17/68; A61B 2017/681
USPC ........................... 606/278, 86 R, 90, 99, 105
See application file for complete search history.

(56) References Cited

U.S. PATENT DOCUMENTS

| 8,206,395 B2 * | 6/2012 | McLean ............. A61B 17/7011 606/86 A |
| 8,398,644 B2 | 3/2013 | Kirschman |
| 2003/0171751 A1 | 9/2003 | Rifland |
| 2007/0270842 A1 | 11/2007 | Bankoski et al. |
| 2008/0045963 A1 | 2/2008 | Abdou |
| 2008/0183045 A1 | 7/2008 | Perez-Cruet et al. |
| 2008/0221626 A1 | 9/2008 | Butters et al. |
| 2008/0262318 A1 | 10/2008 | Gorek et al. |
| 2008/0300465 A1 | 12/2008 | Feigenwinter et al. |
| 2009/0036746 A1 | 2/2009 | Blackwell et al. |
| 2009/0088604 A1 | 4/2009 | Lowry et al. |

(Continued)

FOREIGN PATENT DOCUMENTS

WO        2010135537        11/2010

OTHER PUBLICATIONS http://www.synthes.com/MediaBin/US%20DATA/Product%20Support%20Materials/Technique%20Guides/SPINE/SPTGMATRIXSpineJ9700D.pdf, p. 5, published on or before May 16, 2013.

(Continued)

*Primary Examiner* — Ellen C Hammond
*Assistant Examiner* — Christina Negrellirodrigue

(57) ABSTRACT

A combined apparatus for compression and distraction of a first physical component having a first bone screw and a second physical component having a second bone screw, said apparatus comprising a connected rod fixedly connected to one of the first and second bone screw heads and slidably connected to the other of the first and second bone screw heads, a rod holder comprising a ramp, and A screw head extension comprising an protruding member and an adjusting means, such that when the protruding member is moved vertically, pressure between said protruding member and progressively wider portions of said ramp force an increase in distance between the rod holder and adjacent bone screw head, resulting in compression or distraction as desired of the physical components.

12 Claims, 4 Drawing Sheets

(56) References Cited

U.S. PATENT DOCUMENTS

| | | | |
|---|---|---|---|
| 2009/0149892 A1* | 6/2009 | Stad | A61B 17/7077 |
| | | | 606/86 A |
| 2009/0221878 A1 | 9/2009 | Gorek | |
| 2010/0198272 A1 | 8/2010 | Keyer | |
| 2011/0034779 A1 | 2/2011 | Louftus et al. | |
| 2011/0130793 A1* | 6/2011 | Woolley | A61B 17/0206 |
| | | | 606/279 |
| 2012/0232350 A1 | 9/2012 | Seex | |
| 2012/0245431 A1* | 9/2012 | Baudouin | A61B 17/0206 |
| | | | 600/213 |

OTHER PUBLICATIONS

Lehman et. al., Standard and Minimally Invasive Approaches to the Spine, http://www.sciencedirect.com/science/article/pii/S0030589805000209 , published 2005.

* cited by examiner

SPINAL COMPRESSOR AND DISTRACTOR

CROSS-REFERENCES TO RELATED APPLICATIONS

This application is a Continuation in Part of U.S. application Ser. No. 14/200,785, Spinal Compressor and Distracior by Dr. John Song, filed on Mar. 7, 2014. Said application is incorporated by reference in its entirety herein.

STATEMENT REGARDING FEDERALLY SPONSORED RESEARCH OR DEVELOPMENT

Not applicable

BACKGROUND

During orthopedic surgical procedures, such as by way of example spinal orthopedic surgery, it is often desirable to use pedicle screws or other bone screws. Such screws can serve a variety of functions, such as stabilizing the spine, fixating two or more vertebrae with respect to each other, or serving as anchor points for various instruments such as rods, retractors, compressors, and distractors.

During orthopedic surgical procedures, it is also often desirable to distract various physical components into locations further separated from each other, such as distracting two vertebrae to increase the space between them. Distraction can be desirable to, among other functions, increase the space between two vertebrae preparatory to the insertion of an implant. In other situations, it is desirable to compress various physical components into locations closer to each other, such as compressing two vertebrae to decrease the space between them. Compression can be desirable to, among other functions, space two vertebrae a desired distance from each other prior to fixating the vertebrae.

In some situations in orthopedic surgery, it is desirable both to distract and to compress various physical components during the same surgical procedure. At times, both distraction and compression are desirable at the same physical location, with respect to the same physical components, at various times during the procedure. In orthopedic spinal surgery, by way of example, compression and/or distraction may be desirable with respect to vertebrae that are to be fixated with pedicle or other bone screws.

Tools adapted to distract physical components such are vertebrae are known to the art. Tools known to the art function in general by providing a pair of tips or ends adapted to fit between the two physical components to be distracted, such as, for example, two vertebrae. Mechanical force is then applied to the handle of the distractor tool, typically by squeezing or rotating. Through lever, screw, or other mechanical action, the distractor tool converts such mechanical force applied to the handle into force pressing the tips or ends of the distractor away from each other. Tools adapted to compress physical components such as vertebrae are similarly known to the art, and work in a similar but largely opposite fashion from distractors. Such compressor tools function generally by providing a pair of tips or ends adapted to fit on or around the outer surfaces of two physical components to be compressed, such as, for example, two vertebrae. Mechanical force is applied to the handle of the compressor tool, typically by squeezing or rotating. Through lever, screw, or other mechanical action, the compressor tool converts such mechanical force applied to the handle into force pressing the tips or ends of the compressor towards each other.

Tools known to the art suffer a number of deficiencies. First, many surgical kits provide a distractor and a compressor as separate tools. This complicates the surgical procedure by requiring the surgeon and other surgical staff to manage and keep track of a larger number of tools. The use of separate tools can also pose problems if one of the tools becomes contaminated and must be removed from the procedure.

Although some tools exist that are capable of both distraction and compression, combined tools known to the art suffer a number of additional disadvantages. For example, combined distractor-compressor tools known to the art require the application of significant mechanical force to achieve distraction or compression. It is often difficult to apply sufficient mechanical force to a combined distractor-compressor tool while keeping the tips or ends of the tool properly located to achieve the desired distraction or compression. Additionally, the risk of tool slippage and resultant injury to the patient is significant. Since such combined tools must often be kept in place to maintain the desired positioning of physical components while screws or other fixation devices are installed, combined tools known to the art can result in a cluttered and difficult-to-navigate surgical opening, resulting in inconvenience and difficulty for the surgeon and an increased risk of poor outcome for the patient.

SUMMARY

Versions of the present invention are directed to a combined distractor-compressor tool apparatus adapted for use in orthopedic surgery, and preferably for use in orthopedic spinal surgery. Versions of the present invention include a combined distractor-compressor tool capable of both distracting and compressing physical components during surgical procedures. The combined tool apparatus of the present invention mounts to screws secured in bone, preferably pedicle screws. Thus, a combined tool apparatus according to the teachings of the present invention reduces the number of tools required to perform a surgical procedure, and, by its connection to installed bone screws, eliminates the risks associated with slippage of the tool when mechanical force is applied. Further, versions of the present invention incorporate rods that can be used as fixation devices. Since the combined tool apparatus of the present invention mounts directly to bone screws, and preferably to bone screw heads, versions of the present invention provide an additional advantage of eliminating the need to install a separate fixation device while attempting to use a distracting or compressing tool.

In one embodiment, the combined tool apparatus of the present invention comprises a distractor wherein a connecting rod is mounted to a first bone screw head and to a second bone screw head, said first and second bone screw heads being installed in bone, wherein the connecting rod is mounted fixedly to the first bone screw head and mounted slidably to the second bone screw head. A rod holder is attached to said connecting rod at a point between a said first bone screw head and said second bone screw head, wherein said rod holder is adjacent to either said first bone screw head or said second bone screw head and is generally co-axial with said first and second bone screw heads. The rod holder comprises a ramp on one face, facing the connecting rod to which the rod holder is nearest. A screw head extension is mounted to the bone screw head to which the rod holder is adjacent by sliding or otherwise connecting said screw head extension over said screw head. The screw head extension is internally threaded. The screw head extension operatively connects to an adjusting member, said adjusting member comprising an externally threaded portion that fits within the internally threaded portion of the screw head extension, and a protruding member protruding outwardly from said threaded portion and rotatably adjustable with respect to the threaded portion. The protruding member is moveable up or down along the longitudinal axis of the screw head extension by rotational adjustment of the adjusting member within the screw head extension. When a portion of the adjusting member is turned, such as by a turning means, the protruding member moves vertically along the longitudinal axis of the screw head extension, placing increasing pressure against the ramp, forcing the first bone screw head and second bone screw head to move away from each other and thus distracting the physical components to which the first and second bone screws are connected.

In another embodiment, the combined tool apparatus comprises a compressor wherein a connecting rod is mounted to a first bone screw head and a second bone screw head, said first and second bone screw heads being installed in bone, wherein the connecting rod is mounted fixedly to the first bone screw head and mounted slidably to the second bone screw head. A rod holder is attached to said connecting rod at a point adjacent to either said first bone screw head or said second bone screw head, but not in between said first and second bone screw heads, and is generally co-axial with said first and second bone screw heads. The rod holder comprises a ramp on one face, facing the bone screw head to which the rod holder is nearest. A screw head extension is mounted to the bone screw head to which the rod holder is adjacent by sliding said screw head extension over said screw head or by other means of connection. The screw head extension is internally threaded. The screw head extension operatively connects to an adjusting member, said adjusting member comprising an externally threaded portion that fits within the internally threaded portion of the screw head extension, and a protruding member protruding outwardly from said threaded portion and rotatably adjustable with respect to the threaded portion. The protruding member is moveable up or down along the longitudinal axis of the screw head extension by rotational adjustment of the adjusting member within the screw head extension. When a portion of the adjusting member is turned, such as by a turning means, the protruding member moves vertically along the longitudinal axis of the screw head extension, placing increasing pressure against the ramp, forcing the first bone screw head and second bone screw head to move towards each other and thus compressing the physical components to which the first and second bone screws are connected.

In the summary above and in the description, and the claims below, and in the accompanying drawings, reference is made to particular features of the invention. It is to be understood that the disclosure of the invention in this specification includes all possible combinations of such particular features.

BRIEF DESCRIPTION OF THE DRAWINGS

These and other features, aspects, and advantages of the present invention will become better understood with regard to the following description and accompanying drawings, where.

DESCRIPTION

Figure 1:
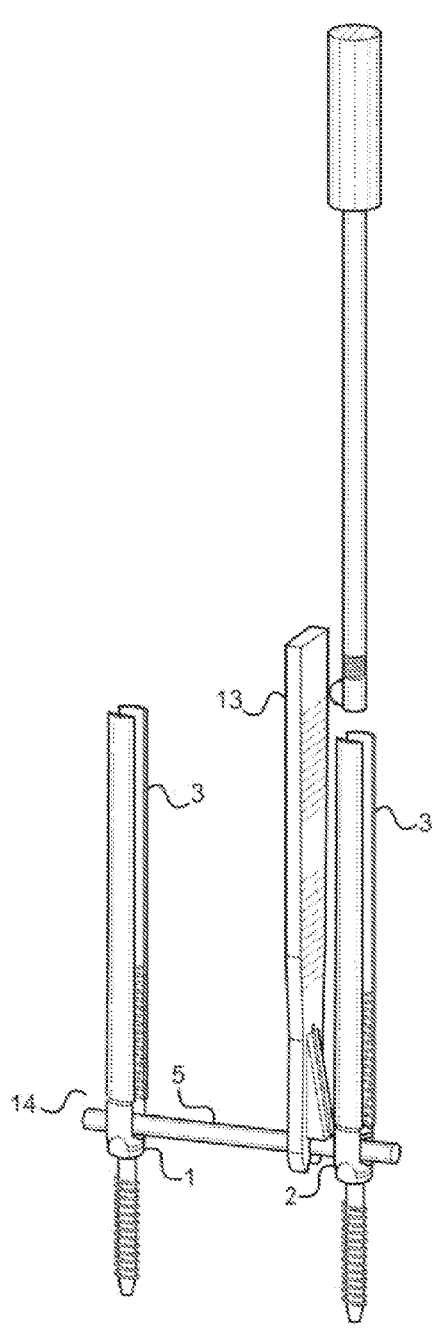
FIG. 1 shows a perspective view of a version of the invention adapted for distraction, in which the screw head extension is mounted to a first bone screw head and a rod holder comprising a ramp is adjacent to the screw head extension.

Embodiments of the present combined tool apparatus are directed towards an apparatus for distraction and compression of physical components during surgery, wherein said apparatus makes use of bone screws installed in the physical components to be distracted or compressed. In preferred embodiments, the combined tool is adapted for use in connection with orthopedic spine surgery, and the bone screws are pedicle screws installed into vertebrae.

A "bone screw" according to the versions of the present invention is, as will be recognized by one skilled in the art, a screw adapted to be fixed to bone. A "bone screw" according to versions of this invention comprises a screw adapted for fixation to bone, and also comprises a screw head, wherein said screw head is an elongated member extending outwardly from said screw and adapted to accommodate connection with a screw head extension [3], as described elsewhere herein. Embodiments of the present invention include a first bone screw and a second bone screw, which comprise a first bone screw head [1] and second bone screw head [2]. Preferably, the first and second bone screws are installed into vertebra, and most, preferably, are installed into adjacent vertebra. Further preferably, the first and second bone screws are pedicle screws. Other forms and types of screws may be used within the scope of this invention, as will be apparent to one skilled in the art.

A "connecting rod" [5] is a rod adapted to mount to at least the first bone screw [1] and second bone screw [2]. Preferably, the connecting rod [5] is adapted to mount to bone screw heads. A connecting rod [5] mounts to at least one of the first and second bone screw heads fixedly, and mounts to at least one of the first and second bone screw heads slidably. Preferably, the connecting rod [5] is a metal rod used for temporary or permanent fixation of vertebrae, such as in a bone fusion procedure, as would be recognized by one skilled in the art.

A fixed mount between said connecting rod [5] and said first or second bone screw head can be accomplished by a variety of mechanical connection means, as will be recognized by one skilled in the art. Preferably, at least one of said first and second bone screw heads comprise in part a collar [7], said collar comprises in part a void [8], and said collar [7] further comprises a set screw [9] such that when said connecting rod [5] is placed in or through said void [8] and said set screw [9] is tightened, said connecting rod [5] and said bone screw head are fixedly connected. As will be appreciated by one skilled in the art, a fixed mount achieved in this manner can be separated by loosening the set screw [9].

A slidable mount between said connecting rod [5] and said first or second bone screw head can be accomplished by a variety of mechanical connection means, as will be recognized by one skilled in the art. Preferably, at least one of said first or second bone screw head comprises in part aperture [11] adapted to allow said connecting rod [5] to pass through said aperture [11] slidably. As will be recognized by one skilled in the art, the collar [7] and aperture [11] can be comprised by the saddle or tulip of bone screws known to the art.

A "rod holder" [13] according to embodiments of the present invention comprises an elongated member adapted at its distal end for removable connection to the connecting rod [5]. A rod holder [13] according to these embodiments of the present invention may connect to said connecting rod [5] by any removable mechanical means, as will be appreciated by one skilled in the art. Preferably, said rod holder [13] in these embodiments is adapted for connection to said connection rod [5] by way of a slot [15] in the distal end of said rod holder [13], said slot [15] adapted to form a friction fit between said rod holder [13] and said connecting rod [5] when the distal end of said rod holder [13] is pressed against said connecting rod [5]. Preferably, in these embodiments said rod holder [13] extends generally coaxially with said first and second bone screw heads when said rod holder [13] is in connection with said connecting rod [5]. The rod holder [13] in a preferred embodiment further comprises a ramp [14]. Preferably, the ramp [14] is located near the distal end of the rod holder [14]. The ramp [14] has a narrowest point that is substantially flush with the rod holder [13] and a widest point that extends outwardly from the rod holder [13]. In a preferred embodiment, the widest point of the ramp is located near the distal end of the rod holder [13], and the narrowest point of the ramp is located proximally to the widest point. Optionally, the widest point of the ramp may be located proximally to the narrowest point. As will be understood by one skilled in the art, the ramp [114] may be located virtually anywhere along the length of the rod holder [13]. Optionally, the rod holder [13] may comprise a protruding member in lieu of a ramp.

A "screw head extension" [3] according to versions of the present invention is an elongated tubular member that is, preferably, internally threaded. A screw head extension [3] comprises an at least partially open tubular member, comprising at least an open portion along a portion of the longitudinal axis of the extension. A screw head extension [3] fits to a first bone screw head or second bone screw head by mechanical connection, and preferably by sliding over the head of a bone screw so that the screw head extension [3] is generally coaxial with the bone screw. A screw head extension [3] is at least partially threaded on its inner face and adapted to accept a cooperatively threaded generally cylindrical adjusting member [100].

An adjusting member [100] is a generally cylindrical member that is at least partially threaded, and preferably cooperatively threaded with the threading on the inner face of a screw head extension [3]. The adjusting member [100] comprises a threaded shaft portion [101], and, preferably, a protruding member [16], wherein the protruding member [16] is rotatably adjustable with respect to the threaded shaft portion [101], and, optionally, a head [18] to facilitate turning of the adjusting member, such as a hex head. The protruding member [16] protrudes outwardly from the longitudinal axis of the screw head extension [3], preferably in the direction of an adjacent rod holder [13]. The protruding member [16] can be any shape conducive to sliding up or down a ramp [14], or, alternately, can comprise a ramp adapted to work cooperatively with a separate protruding member located on an adjacent rod holder [13]. In embodiments where the protruding member is not a ramp, the extending portion of the protruding member [16] is preferably a semicircular shape. When the adjusting member [100] is placed within a screw head extension [3], the protruding member [16] extends outwardly from the screw head extension [3] through a longitudinal opening in the body of the screw head extension [3]. When the adjusting member [100] and screw head extension are assembled, the protruding member [16] can be located at any point along the length of the screw head extension [3], although preferably the range of movement of the protruding member [16] corresponds to, at one end, the narrowest point of the ramp [14] and, at the other end, the widest point of the ramp [14] when the rod holder [13] is connected to the connecting rod. The protruding member [16] is adjustable vertically up or down along at least a portion of the screw head extension [3] by rotatable adjustment of the threaded shaft portion of the adjusting member [100] within the cooperative threading of the screw head extension [3]. In a preferred embodiment, the screw head extension [3] and adjusting member [100], when assembled in threaded connection, comprise a screw drive, wherein turning of the adjusting member [100] results in vertical movement of the protruding member [16] with respect to the ramp [14], as will be appreciated by one skilled in the art. As will be appreciated by one skilled in the art, other suitable means for adjustment of the protruding member [16] vertically within the screw head extension may be employed, including cranks, ratchets, swashplates, and the like.

Figure 4:
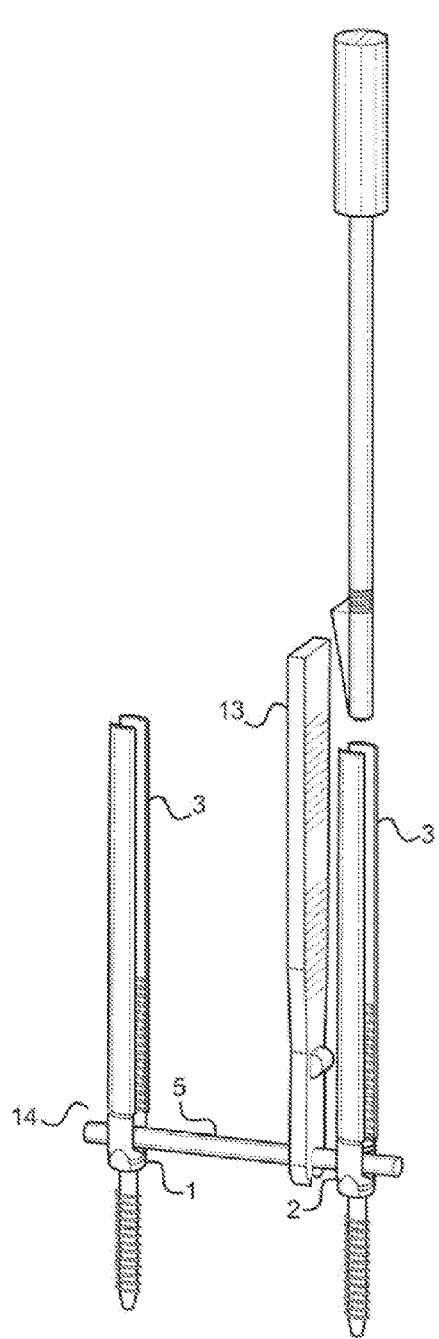
FIG. 4 shows a perspective view of a version of the invention adapted for distraction, in which the adjusting member comprises a ramp and the rod holder comprises a protruding member.
Figure 5:
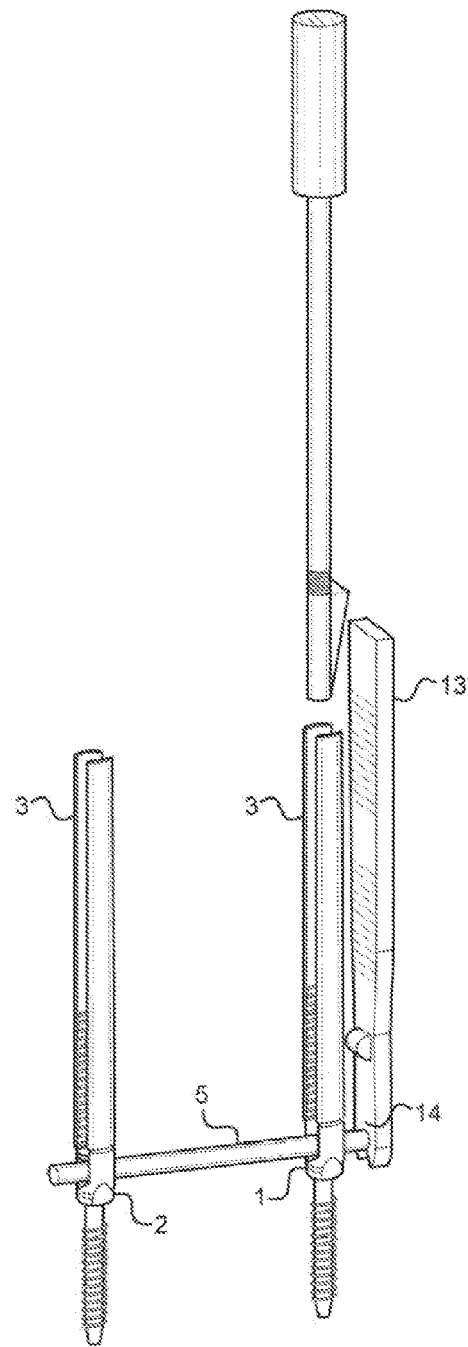
FIG. 5 shows a perspective view of a version of the invention adapted for compression, in which the adjusting member comprises a ramp and the rod holder comprises a protruding member.
Figure 6:
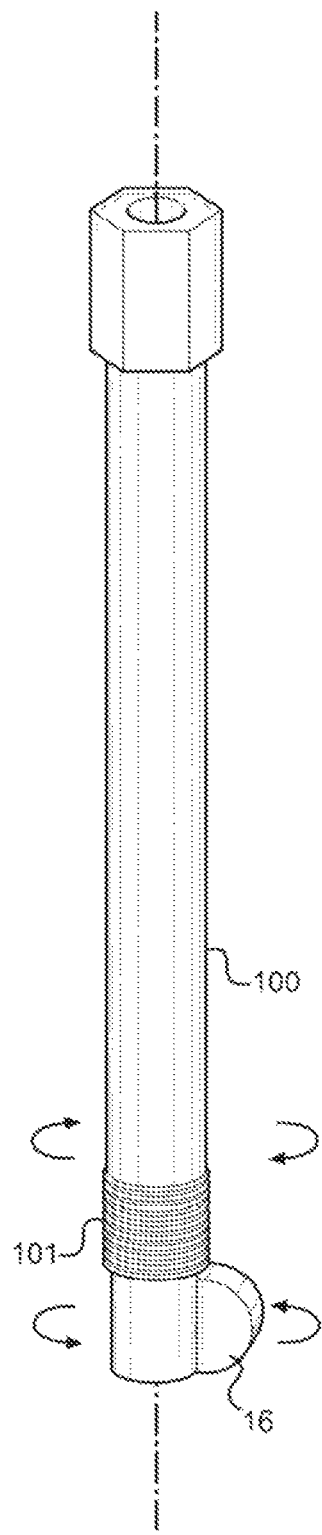
FIG. 6 shows a side view of an adjusting member according to version of the present invention as depicted in FIGS. 1 and 2.

In alternative embodiments, the adjusting member may comprise, as a protruding member, a ramp [104] extending outwardly from the face of the adjusting member. In these embodiments, as depicted in FIGS. 4 and 5, the rod holder [102] comprises a protruding member [16] that works cooperatively with the ramp [104] to compress or distract, as desired, when the ramp [104] is moved up or down by way of the adjusting member.

In still alternative embodiments, the rod holder [102] may comprise an elongated tubular member that is, preferably, threaded on its interior face. In these embodiments, the rod holder [102] comprises an at least partially open tubular member, comprising at least an open portion along a portion of the longitudinal axis of the rod holder. The rod holder [102] in these embodiments fits to a first bone screw head or second bone screw head by connection of the rod holder [102] to the connecting rod [5] via a slot [15] so that the rod holder [102] is generally coaxial with the bone screw. A rod holder [102] in these embodiments is at least partially threaded on its inner face and adapted to accept a cooperatively threaded generally cylindrical adjusting member [100]. In these embodiments, compression and distracting is achieved by the same action as in the embodiments depicted in FIGS. 1 and 2, however, a ramp [14] is located on the bone screw head extension [103] and the adjusting member [100] connects cooperatively and rotatably adjustably with the rod holder [102].

As depicted in FIG. 1, in one embodiment the combined tool apparatus comprises a distractor in which a connecting rod [5] is mounted slidably to a first bone screw head [1] and fixedly to a second bone screw head [2], said bone screws being installed in bone. A rod holder [13] is attached to said connecting rod [5] at a point between a said first bone screw head [1] and said second bone screw head [2], wherein said rod holder [13] is generally adjacent to said first or second bone screw head and generally co-axial with said first and second bone screw heads. The rod holder [13] comprises a ramp [14] near its distal end. The narrowest point of the ramp [14] is substantially flush with the surface of the rod holder and is proximal to the widest end of the ramp, said widest end protruding towards to the bone screw head to which the rod holder is adjacent. A screw head extension [3] is mounted to the bone screw head to which the rod holder [13] is adjacent by sliding said screw head extension [3] over said screw head. An adjusting member [100] comprising a threaded shaft member [101] and a protruding member [16] is connected to the screw head extension [3] adjacent the rod holder [13] by threaded engagement of the threaded shaft portion [101] with the threading on the interior face of the screw head extension [3] such that the protruding member [16] protrudes and extends generally towards the rod holder [13] at a vertical location substantially corresponding to the location of the ramp [14]. When the adjusting member [100] is rotated within the screw head extension [3], the protruding member [16] moves distally along the longitudinal axis of the adjustment member [3]. The protruding member [16] presses against the ramp [14] as it moves towards progressively wider portions of the ramp, forcing the first bone screw head [1] and second bone screw head [2] to move away from each other and distracting the physical components to which the first and second bone screws are connected.

Figure 2:
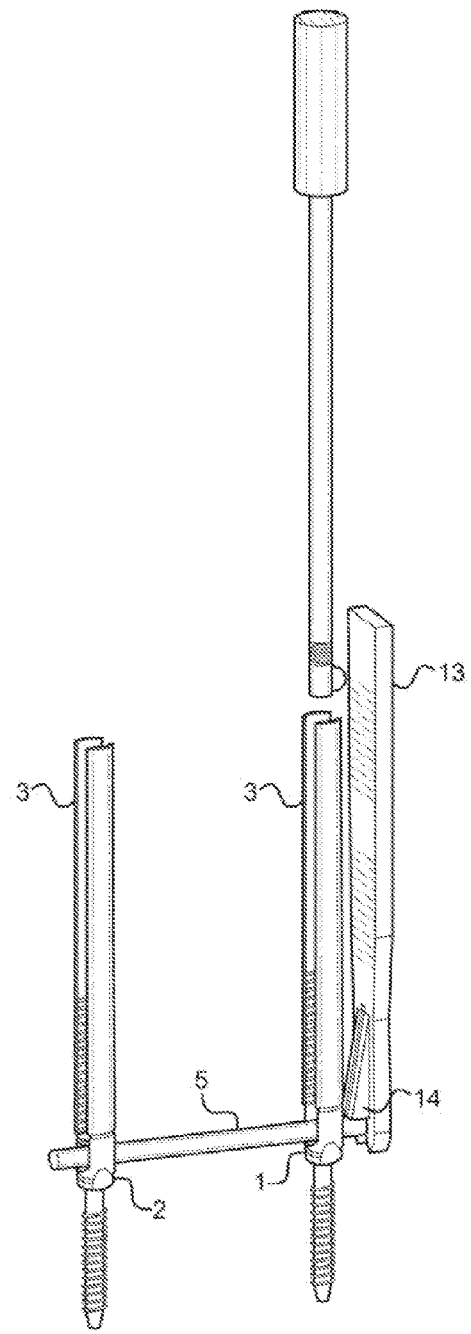
FIG. 2 shows a perspective view of a version of the invention adapted for compression, in which the screw head extension is mounted to a first bone screw head and a rod holder comprising a ramp is adjacent to the screw head extension.
Figure 3:
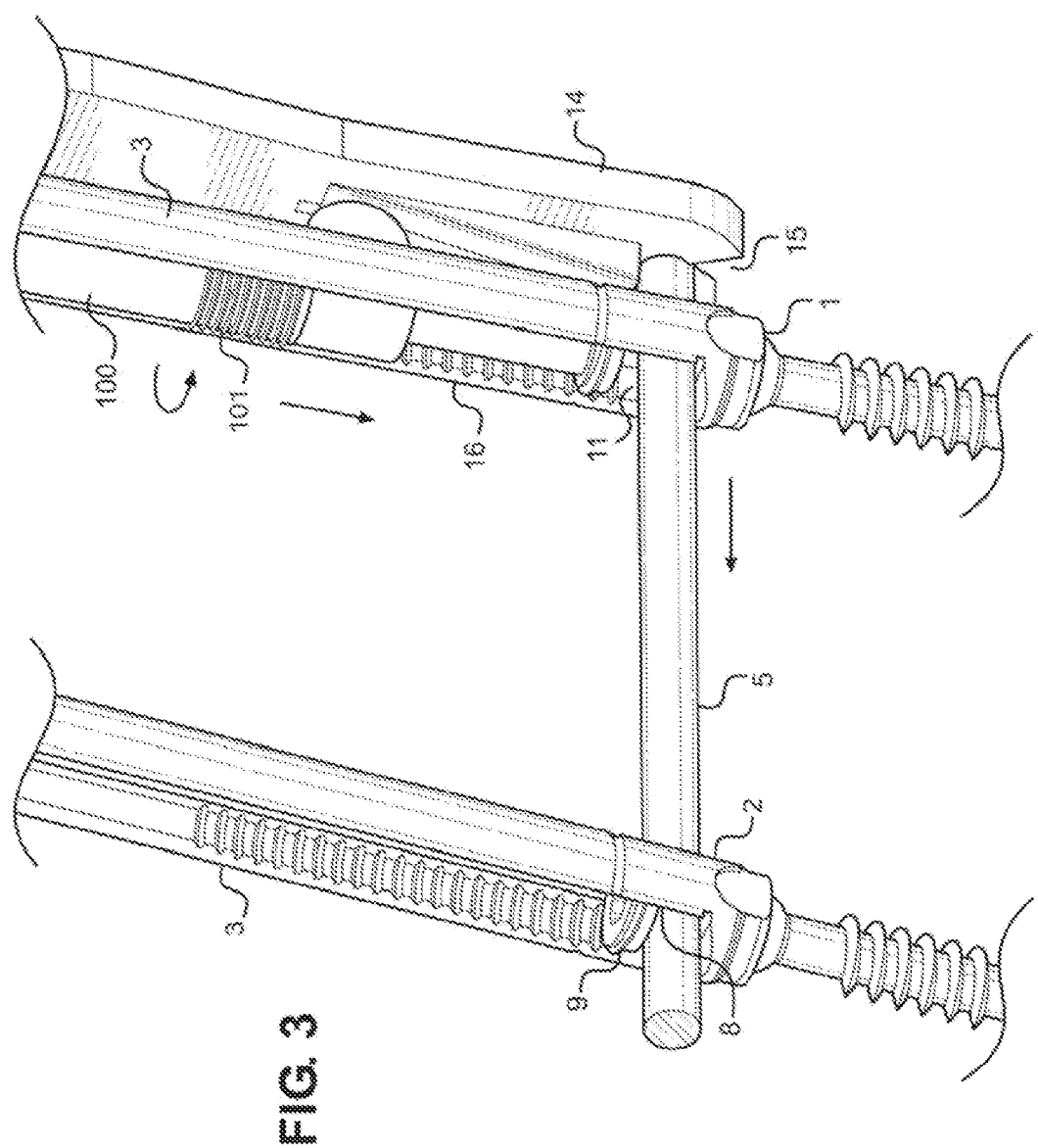
FIG. 3 shows a close-up view of a portion of the device as depicted in FIG. 2.

As depicted in FIG. 2, in another embodiment the combined tool apparatus comprises a compressor wherein a connecting rod [5] is mounted to at least a first bone screw head [1] and a second bone screw head [2], said bone screws being installed in bone, wherein the connecting rod [5] is mounted slidably to the first bone screw head [1] and mounted fixedly to the second bone screw head [2]. A rod holder [13] is attached to said connecting rod [5] at a point adjacent to either first bone screw head [1] or said second bone screw head [2] but not in between said first and second bone screw heads, and is generally co-axial with said first and second bone screw heads. The rod holder [13] comprises a ramp [14] near its distal end. The narrowest point of the ramp [14] is substantially flush with the surface of the rod holder and is proximal to the widest end of the ramp, said widest end protruding towards to the bone screw head to which the rod holder is adjacent. A screw head extension [3] is mounted to the bone screw head to which the rod holder [13] is adjacent by sliding said screw head extension [3] over said screw head. An adjusting member [100] comprising a threaded shaft member [101] and a protruding member [16] is connected to the screw head extension [3] adjacent the rod holder [13] by threaded engagement of the threaded shaft portion [101] with the threading on the interior face of the screw head extension [3] such that the protruding member [16] protrudes and extends generally towards the rod holder [13] at a vertical location substantially corresponding to the location of the ramp [14]. When the adjusting member [100] is rotated within the screw head extension [3], the protruding member [16] moves distally along the longitudinal axis of the adjustment member [3]. The protruding member [16] presses against the ramp [14] as it moves towards progressively wider portions of the ramp, forcing the first bone screw head [1] and second bone screw head [2] to move away from each other and compressing the physical components to which the first and second bone screws are connected.

As depicted in FIG. 4, in another embodiment the combined tool apparatus comprises a distractor in which a connecting rod [5] is mounted to a first bone screw head [1] and a second bone screw head [2], said first and second bone screw heads being installed in bone, wherein the connecting rod [5] is mounted slidably to the first bone screw head [1] and mounted fixedly to the second bone screw head [2]. A rod holder [102] is attached to said connecting rod [5] at a point in between a said first bone screw head [1] and said second bone screw head [2], wherein said rod holder [102] is adjacent to said first bone screw head or said second bone screw head and is generally co-axial with said first and second bone screw heads. An adjusting member is attached to a bone screw head adjacent to the rod holder [102], said adjusting member comprising a ramp [104] near its distal end. The narrowest point of the ramp is substantially flush with the surface of the screw head extension [103] and is proximal to the widest end of the ramp, said widest end extending generally towards the adjacent rod holder [102]. The rod holder comprises a protruding member [16] positioned to work cooperatively with the ramp [104]. An adjusting member [100] comprising a threaded shaft member [101] and a protruding member [16] is connected to the screw head extension [103] by threaded engagement of the threaded shaft portion [101] with the threading on the interior face of the screw head extension [103] such that the ramp [104] protrudes from the screw head extension [103] and extends generally towards the rod holder [13] at a vertical location substantially corresponding to the location of protruding member protruding from the rod holder [13]. When the adjusting member [100] is rotated within the screw head extension [103], the ramp [104] moves distally along the longitudinal axis of the screw head extension [103]. The protruding member [16] thus presses against the ramp [104] as it moves towards progressively wider portions of the ramp [104], forcing the first bone screw head [1] and second bone screw head [2] to move away from each and distracting the physical components to which the first and second bone screws are connected.

As depicted in FIG. 5, in another embodiment the combined tool apparatus comprises a compressor, wherein a connecting rod [5] is mounted to a first bone screw head [1] and a second bone screw head [2], said first and second bone screw heads being installed in bone, wherein the connecting rod [5] is mounted slidably to the first bone screw head [1] and mounted fixedly to the second bone screw head [2]. A rod holder [102] is attached to said connecting rod [5] at a point adjacent to either first bone screw head [1] or said second bone screw head [2], but not in between said first and second bone screw heads, and is generally co-axial with said first and second bone screw heads. An adjusting member is attached to a bone screw head adjacent to the rod holder [102], said adjusting member comprising a ramp [104] near its distal end. The narrowest point of the ramp is substantially flush with the surface of the screw head extension [103] and is proximal to the widest end of the ramp, said widest end extending generally towards the adjacent rod holder [102]. The rod holder comprises a protruding member [16] positioned to work cooperatively with the ramp [104]. An adjusting member [100] comprising a threaded shaft member [101] and a protruding member [16] is connected to the screw head extension [103] by threaded engagement of the threaded shaft portion [101] with the threading on the interior face of the screw head extension [103] such that the ramp [104] protrudes from the screw head extension [103] and extends generally towards the rod holder [13] at a vertical location substantially corresponding to the location of protruding member protruding from the rod holder [13]. When the adjusting member [100] is rotated within the screw head extension [103], the ramp [104] moves distally along the longitudinal axis of the screw head extension [103]. The protruding member [16] thus presses against the ramp [104] as it moves towards progressively wider portions of the ramp [104], forcing the first bone screw head [1] and second bone screw head [2] to move towards from each other, compressing the physical components to which the first and second bone screws are connected.

Although the present invention has been described in considerable detail with reference to certain preferred versions thereof, other versions are possible. For example, other screws, materials, connection means, turning means, or adjusting means may be used than those described in detail. Similarly, other placements of the versions of the invention may be employed than those shown in detail, and the invention may be used to compress or distract physical components other than those described herein. For example, the ramp may be located proximally rather than distally, or may have its widest end proximal to its distal end, and the protruding member may be adjusted vertically by means other than a screw mechanism. Therefore, the spirit and scope of the claims should not be limited to the description of the preferred versions described herein.

What is claimed is:

1. A combined tool apparatus for compression or distraction of a first physical component having a first bone screw and a second physical component having a second bone screw, said apparatus comprising:
    a. a first bone screw implanted in a first physical component and a second bone screw implanted in a second physical component, each of said first bone screw and said second bone screw comprising a screw, a collar, and a screw head;
    b. a connecting rod mounted fixedly to said at least one of said first bone screw and said second bone screw and mounted slidably to the other of said first bone screw and said second bone screw;
    c. a rod holder attached to said connecting rod at a location adjacent to said first bone screw at a location not in between said first bone screw and said second bone screw, said rod holder comprising a ramp extending orthogonally to the longitudinal axis of said rod holder in the general direction of said first bone screw;
    d. A screw head extension connected to said first bone screw, said screw head extension comprising two or more prongs defining an a cylinder with at least one slit along its longitudinal axis and at least partially threaded on its interior face;
    e. an adjusting member comprising a threaded portion and a protruding member, wherein said protruding member rotates freely with respect to said adjusting member threaded portion, said adjusting member threaded portion connected threadedly to said screw head threaded portion, and said protruding member fits and moves axially with said slit, such that turning said adjusting member with respect to said screw head extension moves said protruding member axially;
    f. wherein axial adjustment of said protruding member in one or more of the distal direction or proximal direction by said adjusting means presses said protruding member against progressively wider portions of said ramp, forcing said screw head extension away from said rod holder and compressing said first physical component and said second physical component.

2. The apparatus of claim 1 wherein said rod holder is detachably attached to said connecting rod.

3. A combined tool apparatus for compression or distraction of a first physical component having a first bone screw and a second physical component having a second bone screw, said apparatus comprising:
    a. a first bone screw implanted in a first physical component and a second bone screw implanted in a second physical component, each of said first bone screw and said second bone screw comprising a screw, a collar, and a screw head;
    b. a connecting rod mounted fixedly to said at least one of said first bone screw and said second bone screw and mounted slidably to at least one of said first bone screw and said second bone screw;
    c. a rod holder attached to said connecting rod adjacent to said first bone screw at a location between said first bone screw and said second bone screw, said rod holder comprising a ramp extending orthogonally from the longitudinal axis of said rod holder in the general direction of said first bone screw;
    d. A screw head extension connected to said first bone screw, said screw head extension comprising two or more prongs defining an a cylinder with at least one slit along its longitudinal axis and at least partially threaded on its interior face;
    e. an adjusting member comprising a threaded portion and a protruding member, wherein said protruding member rotates freely with respect to said adjusting member threaded portion, said adjusting member threaded portion connected threadedly to said screw head threaded portion, and said protruding member fits and moves axially with said slit, such that turning said adjusting member with respect to said screw head extension moves said protruding member axially;
    f. wherein axial adjustment of said protruding member in one or more of the distal direction or proximal direction by said adjusting means presses said protruding member against progressively wider portions of said ramp, forcing said screw head extension away from said rod holder and distracting said first physical component and said second physical component.

4. The apparatus of claim 3 wherein said rod holder is detachably attached to said connecting rod.

5. A combined tool apparatus for compression or distraction of a first physical component having a first bone screw and a second physical component having a second bone screw, said apparatus comprising:
    a. a first bone screw implanted in a first physical component and a second bone screw implanted in a second physical component, each of said first bone screw and said second bone screw comprising a screw, a collar, and a screw head;
    b. a connecting rod mounted fixedly to said at least one of said first bone screw and said second bone screw and mounted slidably to at least one of said first bone screw and said second bone screw;
    c. a rod holder attached to said connecting rod adjacent to said first bone screw at a location between said first bone screw and said second bone screw, said rod holder comprising a protruding member, wherein said protruding member protrudes generally orthogonally from said rod holder in the general direction of said first bone screw;

d. A screw head extension connected to said first bone screw, said screw head extension comprising two or more prongs defining an a cylinder with at least one slit along its longitudinal axis and at least partially threaded on its interior face;
e. an adjusting member comprising a threaded portion and a ramp, wherein said ramp rotates freely with respect to said adjusting member threaded portion, said adjusting member threaded portion connected threadedly to said screw head threaded portion, and said ramp fits and moves axially with said slit, such that turning said adjusting member with respect to said screw head extension moves said ramp member axially;
f. wherein axial adjustment of said ramp in one or more of the distal direction or proximal direction by said adjusting means presses said protruding member against progressively wider portions of said ramp, forcing said screw head extension away from said rod holder and distracting said first physical component and said second physical component.

6. The apparatus of claim 5 wherein said rod holder is detachably attached to said connecting rod.

7. A combined tool apparatus for compression or distraction of a first physical component having a first bone screw and a second physical component having a second bone screw, said apparatus comprising:
a. a first bone screw implanted in a first physical component and a second bone screw implanted in a second physical component, each of said first bone screw and said second bone screw comprising a screw, a collar, and a screw head;
b. a connecting rod mounted fixedly to said at least one of said first bone screw and said second bone screw and mounted slidably to at least one of said first bone screw and said second bone screw;
c. a rod holder attached to said connecting rod adjacent to said first bone screw at a location not between said first bone screw and said second bone screw, said rod holder comprising a protruding member wherein said protruding member protrudes generally orthogonally from said rod holder in the general direction of said first bone screw;
d. A screw head extension connected to said first bone screw, said screw head extension comprising two or more prongs defining an a cylinder with at least one slit along its longitudinal axis and at least partially threaded on its interior face;
e. an adjusting member comprising a threaded portion and a ramp, wherein said ramp rotates freely with respect to said adjusting member threaded portion, said adjusting member threaded portion connected threadedly to said screw head threaded portion, and said ramp fits and moves axially with said slit, such that turning said adjusting member with respect to said screw head extension moves said ramp member axially;
f. wherein axial adjustment of said ramp in one or more of the distal direction or proximal direction by said adjusting means presses said protruding member against progressively wider portions of said ramp, forcing said screw head extension away from said rod holder and distracting said first physical component and said second physical component.

8. The apparatus of claim 7 wherein said rod holder is detachably attached to said connecting rod.

9. A combined tool apparatus for compression or distraction of a first physical component having a first bone screw and a second physical component having a second bone screw, said apparatus comprising:
a. a first bone screw implanted in a first physical component and a second bone screw implanted in a second physical component, each of said first bone screw and said second bone screw comprising a screw, a collar, and a screw head;
b. a connecting rod mounted fixedly to said at least one of said first bone screw and said second bone screw and mounted slidably to the other of said first bone screw and said second bone screw;
c. a rod holder attached to said connecting rod at a location adjacent to said first bone screw at a location not in between said first bone screw and said second bone screw, said rod holder comprising an axially adjustable protruding member comprising a ramp, said ramp protruding generally orthogonally to the longitudinal axis of said rod holder in the general direction of said first bone screw head extension;
d. A first screw head extension connected to said first bone screw, said first screw head extension comprising two or more prongs defining an a cylinder with at least one slit along its longitudinal axis;
e. wherein adjustment of said protruding member in one or more of the distal direction or proximal direction presses progressively wider portions of said ramp against said first screw head extension, forcing said first screw head extension away from said rod holder and compressing said first physical component and said second physical component.

10. The apparatus of claim 9 wherein said rod holder is detachably attached to said connecting rod.

11. A combined tool apparatus for compression or distraction of a first physical component having a first bone screw and a second physical component having a second bone screw, said apparatus comprising:
a. a first bone screw implanted in a first physical component and a second bone screw implanted in a second physical component, each of said first bone screw and said second bone screw comprising a screw, a collar, and a screw head;
b. a connecting rod mounted fixedly to said at least one of said first bone screw and said second bone screw and mounted slidably to the other of said first bone screw and said second bone screw;
c. a rod holder attached to said connecting rod at a location adjacent to said first bone screw at a location in between said first bone screw and said second bone screw, said rod holder comprising an axially adjustable protruding member comprising a ramp, protruding generally orthogonally to the longitudinal axis of said rod holder in the general direction of said first bone screw head extension;
d. A first screw head extension connected to said first bone screw, said first screw head extension comprising two or more prongs defining an a cylinder with at least one slit along its longitudinal axis;
e. wherein adjustment of said protruding member in one or more of the distal direction or proximal direction presses progressively wider portions of said protruding member against said first screw head extension, forcing said first screw head extension away from said rod holder and distracting said first physical component and said second physical component.

12. The apparatus of claim 10 wherein said rod holder is detachably attached to said connecting rod.

\* \* \* \* \*